US009433342B2

(12) United States Patent
Perretta et al.

(10) Patent No.: US 9,433,342 B2
(45) Date of Patent: Sep. 6, 2016

(54) ENDOSCOPIC INSTRUMENT SYSTEM (75) Inventors: Silvana Perretta, Strasbourg (FR); Bernard Dallemagne, Beauafys (BE); Uwe Bacher, Tuttlingen (DE); Sabine Zahler, Ebersberg (DE); Sebastian Wagner, Bretten (DE)

(73) Assignee: Karl Storz GmbH & Co. KG, Tuttlingen (DE)

(*) Notice: Subject to any disclaimer, the term of this patent is extended or adjusted under 35 U.S.C. 154(b) by 165 days.

(21) Appl. No.: 13/312,477

(22) Filed: Dec. 6, 2011

(65) Prior Publication Data
US 2012/0172663 A1 Jul. 5, 2012

(30) Foreign Application Priority Data
Dec. 6, 2010 (DE) .................. 10 2010 053 410
Nov. 29, 2011 (EP) ..................... 11009419

(51) Int. Cl.
*A61B 1/04* (2006.01)
*A61B 1/018* (2006.01)
(Continued)

(52) U.S. Cl.
CPC ............ *A61B 1/018* (2013.01); *A61B 1/005* (2013.01); *A61B 17/062* (2013.01); *A61B 2017/00296* (2013.01); *A61B 2017/00305* (2013.01); *A61B 2017/2919* (2013.01)

(58) Field of Classification Search
CPC ............ A61B 1/018; A61B 1/00071; A61B 1/00119
USPC ............... 600/104, 139, 140, 144, 153, 154; 348/45, 65; 604/508, 510
See application file for complete search history.

(56) References Cited

U.S. PATENT DOCUMENTS

2002/0111534 A1   8/2002   Suzuki et al.
2005/0182292 A1*  8/2005   Suzuki .................. 600/104
(Continued)

FOREIGN PATENT DOCUMENTS

DE        19520717 A1    12/1996
DE    102005049021 A1     4/2007
(Continued)

OTHER PUBLICATIONS

German Search Report; Application No. 10 2010 053 410.2; Issued: Jun. 8, 2011; 5 pages.
(Continued)

*Primary Examiner* — Anhtuan T Nguyen
*Assistant Examiner* — Timothy J Neal
(74) *Attorney, Agent, or Firm* — Whitmyer IP Group LLC (57) ABSTRACT

An endoscopic instrument system for performing endoscopic interventions via a natural access path, including a flexible endoscope with an endoscope handle and an elongate endoscope shaft introducible into a hollow space in a body, wherein the endoscope shaft includes a steerable end section and at least one instrument channel, and also includes an endoscopic instrument with a handle, an elongate instrument shaft and a tool which can be actuated by a pull and/or push element arranged within the instrument shaft and connected to the handle and to the tool, wherein the endoscopic instrument can be introduced into the instrument channel for conducting manipulations in the hollow space in the body, and wherein the instrument shaft includes a continuous flexible tube that is connected, such that it is rotationally fixed, to the handle and to the tool with respect to a longitudinal direction of the tube.

20 Claims, 3 Drawing Sheets

(51) Int. Cl.
*A61B 1/005* (2006.01)
*A61B 1/00* (2006.01)
*A61B 17/062* (2006.01)
*A61B 17/00* (2006.01)
*A61B 17/29* (2006.01)

(56) References Cited

U.S. PATENT DOCUMENTS

| | | | |
|---|---|---|---|
| 2006/0025750 A1* | 2/2006 | Starksen | A61B 17/00234 604/510 |
| 2007/0129719 A1* | 6/2007 | Kendale et al. | 606/41 |
| 2007/0167685 A1* | 7/2007 | Watanabe | 600/154 |
| 2007/0270752 A1* | 11/2007 | LaBombard | 604/164.01 |
| 2008/0064929 A1* | 3/2008 | Wiedenbein | 600/131 |
| 2008/0269562 A1 | 10/2008 | Marescaux et al. | |
| 2009/0023989 A1* | 1/2009 | Honda et al. | 600/106 |
| 2009/0054733 A1 | 2/2009 | Marescaux et al. | |
| 2009/0247820 A1* | 10/2009 | Nomura et al. | 600/104 |
| 2009/0281376 A1* | 11/2009 | Acosta et al. | 600/104 |
| 2009/0318764 A1* | 12/2009 | Yoshimoto | 600/140 |

FOREIGN PATENT DOCUMENTS

| | | |
|---|---|---|
| DE | 102008053880 A1 | 12/2009 |
| DE | 102009007722 A1 | 8/2010 |
| DE | 102009022118 A1 | 11/2010 |
| EP | 1987789 A1 | 11/2008 |

OTHER PUBLICATIONS www.wikipedia.de, headword "Notes", of Dec. 6, 2010; 1 page.
European Search Report; Applicaiton No. EP 11 00 9419; Issued: Feb. 24, 2012; Mailing Date: Mar. 5, 2012; 7 pages.

* cited by examiner

ENDOSCOPIC INSTRUMENT SYSTEM

CROSS-REFERENCE TO RELATED APPLICATIONS

The present application claims priority of German patent application No. 10 2010 053 410.2 filed on Dec. 6, 2010. The present application also claims priority of European patent application No. 11009419.0 filed on Nov. 29, 2011. All prior applications are herein incorporated by reference.

FIELD OF THE INVENTION

The present invention relates to an endoscopic instrument system, in particular for performing endoscopic interventions via a natural access path.

BACKGROUND OF THE INVENTION

Endoscopic operation techniques have become accepted for a multitude of surgical interventions. As opposed to conventional open operations, a substantial advantage of endoscopic operations is that a large incision into the skin and into subjacent tissue for making the surgical field accessible can be dispensed with, in which way a considerable strain of the patient can be avoided and the duration of in-patient treatment can be reduced. Instead, for example in endoscopic interventions in the abdominal cavity, endoscopes and/or endoscopic instruments are introduced through one or several shorter incisions towards the surgical field, where, for example by gas insufflation, a hollow space can be created, within which the surgical manipulations required for performing the intervention, can be conducted. After conducting the manipulations, the endoscopes and/or endoscopic instruments are removed from the abdominal cavity and the cut-through tissue layers are closed, for example by surgical sutures. Although the incisions and therefore the required sutures are relatively short in such laparoscopic interventions, nevertheless possibly scars may remain.

In order to further reduce the patient's strain in surgical interventions in the abdominal cavity, a surgical technique has been developed known under the term NOTES (Natural Orifice Transluminal Endoscopic Surgery), in which the endoscopes and/or endoscopic instruments are introduced through natural orifices such as the pharynx, the esophagus and the stomach (see www.wikipedia.de, headword "NOTES", of Dec. 6, 2010). Through a small incision in the stomach wall, the actual surgical field in the abdominal cavity, for example the gall bladder, can be accessed. As the stomach wall comprises fewer pain receptors than normal skin, in this way the administration of anesthetics can be reduced, further reducing the patient's recovery time. Moreover, the effect of gastric acid can be employed for the prevention of infections. Finally, visible scars can be completely or, if an additional endoscopic access through the body surface is necessitated, at least partially avoided. Endoscopes for performing operations according to the NOTES method are known, for example, from the published applications US 2008/0269562 A1 and US 2009/0054733 A1, which are herewith included in the present application by reference.

After the manipulations inside the abdominal cavity have been performed and the endoscopes and/or endoscopic instruments have been removed from the surgical field, the incision in that organ that constitutes the natural access, for example in the wall of the stomach, is to be closed again. During the actual surgical intervention it may be necessary as well to close tissue openings and/or to connect tissue margins to each other. For this purpose, various techniques are known, such as, for example, clips, tissue anchors, or clamps. However, such techniques not only involve considerable instrumental complexity, but also exhibit the disadvantage, for example, that after the operation at first there remains a foreign body which, due to its mechanical properties, may obstruct the normal function of the stomach wall. Moreover, possible applications of such closing means are limited. Closing the entrance port is thus a problem which so far is not satisfactorily solved in the NOTES method. The incision in the wall of the access organ therefore frequently is not closed at all.

Thus, it would be desirable if an endoscopic instrument system for performing operations via a natural access path (NOTES) were available which is improved in respect to closing the incision in the wall of the access organ. Such closing could be performed, in particular, by a surgical suture of that kind employed for closing an incision in the body surface or in soft tissue close to the surface. The feasibility of providing a suture within such an operation, however, has been very limited up to now.

For providing such sutures, in particular, in operations which can be performed with rigid endoscopes, needle holders for gripping surgical needles are known. These may be designed straight, straight with a curved tip, curved, or part-circular, and are moved approximately on a circular trajectory for performing a stitch and for pulling a surgical thread through the tissue margins to be connected to each other. In order to accomplish this, depending on the kind and the thickness of the tissue and on the kind of the needle, a considerable angular momentum may be required.

Within the framework of the NOTES method flexible endoscopic instruments are employed. In order to increase the rotational stiffness of the shaft, it may be, for example, designed as a wire spiral or be provided with another kind of reinforcement. Nevertheless, in known endoscopic instruments to be employed in flexible endoscopes for performing an operation according to the NOTES method, the angular momentum that can be transferred frequently is not sufficient for a corresponding handling for piercing tissue with a surgical needle, due to the flexibility of the instrument. In other kinds of manipulations, for example for cutting hard tissues, the force and/or the angular momentum that can be exerted with such instruments is not always sufficient for a rapid and safe accomplishment of the operation.

SUMMARY OF THE INVENTION

It is an object of the present invention to provide an endoscopic instrument system, in particular for performing an endoscopic operation through a natural access, that avoids the disadvantages mentioned and by which, in particular, the provision of a surgical suture for closing the entrance port in the access organ is improved.

This object is met by an endoscopic instrument system for performing endoscopic interventions via a natural access path.

According to the invention, an endoscopic instrument system that, in particular, is suitable for conducting endoscopic interventions via a natural access path comprises a flexible endoscope with an endoscope handle and an elongate endoscope shaft which can be introduced into a hollow organ forming the natural access path. Moreover, the endoscope shaft can be suitable for being further introduced into the body, for example into the abdominal cavity, through an incision in the wall of the hollow organ. The endoscope shaft comprises a steerable end section, in particular a deflectable end section. Moreover, the endoscope shaft comprises at least one instrument channel arranged within the endoscope shaft and designed continuous from a proximal (i.e. situated close to a user) end portion to a distal (i.e. situated at a distance from the user) end portion of the endoscope shaft.

Furthermore, the flexible endoscope may comprise optics for capturing and transmitting an endoscopic image from the distal to the proximal end portion of the endoscope, the optics comprising, in particular, an objective and a light guide, for example an ordered glass fiber bundle. The proximal end of the endoscope, in particular the endoscope handle, can be provided with a camera connector, or a camera module may be connected to the proximal end of the endoscope for receiving the endoscopic image transmitted. However, an electronic image sensor may be arranged in the distal end portion of the endoscope shaft as well. Moreover, the endoscope may comprise a light source or a light connector and illumination optics for illuminating the cavity within the body and/or the surgical field. Furthermore, one or several further instrument channels may be provided as well as suction and irrigation connectors and control means for controlling the steerable end section of the endoscope shaft, which are in particular arranged at the endoscope handle and/or at the camera module. An endoscope suitable for conducting endoscopic interventions via a natural access path according to the NOTES method may also comprise cover flaps arranged at the distal end of the endoscope shaft which may form an obturator for introducing the endoscope via the natural access path and through an incision in the access organ and/or which may serve for steering endoscopic instruments introduced through the endoscope shaft.

The endoscopic instrument system furthermore comprises an endoscopic instrument, comprising a handle, an instrument shaft and a tool. The tool can be operated by a pull and/or push element arranged within the instrument shaft and connected to the handle. Preferably, the pull and/or push element is designed as a pull element for exerting a tensile force, however, it may as well be designed as a push element for exerting a compressive force or may be designed for exerting a tensile as well as a compressive force. For conducting manipulations in the hollow space in the body into which the endoscope can be introduced, the endoscopic instrument is introducible into the instrument channel. In particular, the length of the instrument shaft can be such that after introducing the endoscopic instrument into the instrument channel of the endoscope, the tool can be advanced a sufficient distance beyond the distal end of the endoscope shaft in order to be able to conduct the manipulations required for an intervention. In this case, the handle may adjoin the proximal end portion of the endoscope shaft or the endoscope handle, or, in order to facilitate handling, it may be placed at a certain distance from the proximal end of the endoscope shaft and/or the endoscope handle.

According to the invention, the instrument shaft exhibits a continuous flexible tube, within which the pull and/or push element for actuating the tool is arranged. In particular, the instrument shaft may consist solely of the continuous flexible tube, however, the instrument shaft may also comprise an additional outer tube or a coating on its outer side, for example. The instrument shaft thus is designed similar to a rigid endoscopic instrument, and, in particular, is not segmented and is not formed by a wound wire, by a tube weakened by fenestration or notches, nor by a fabric. Due to its design, in particular due to its small outer diameter and/or due to employing elastic high-strength material, the continuous tube is sufficiently flexible for being used in a flexible endoscope. The continuous flexible tube is connected, such that it is rotationally fixed, to the handle as well as to the tool with respect to a longitudinal direction of the tube. The handle therefore not only permits actuating the tool by means of the pull and/or push element and shifting the tool in a longitudinal direction of the instrument shaft, i.e. in a longitudinal direction of the endoscope shaft, but also rotating the tool with respect to a longitudinal axis of the tube, i.e. with respect to a longitudinal axis of the instrument shaft and the endoscope shaft, respectively. The inventive endoscopic instrument system may comprise further instruments designed in a similar or in a different manner for conducting a surgical intervention.

Due to the fact that the instrument shaft comprises a continuous tube, a particularly high rotational stiffness of the instrument shaft is achieved, enabling a particularly precisely steerable rotational motion of the tool with respect to a longitudinal axis of the instrument shaft and the transmission of a particularly high torque from the handle to the tool. In this way, conducting surgical manipulations in a multiplicity of applications is facilitated, for example for cutting hard tissue. Due to the continuous tube being flexible, a combination with the flexible endoscope is made possible, and thus, in particular, an application within the NOTES method.

According to a preferred embodiment of the invention, the tool is designed for holding a surgical needle. Usually, surgical needles provided for closing incisions in endoscopic interventions are designed half-round or part-circular. A needle of this kind is known from the published German patent application DE 10 2009 007 722 A1, for example, which in this respect is included in the present application by reference. For puncturing by the tip of such a needle, the needle usually is gripped by a needle holder in a central or rear portion, i.e. in a portion of the needle distant from the tip of the needle, in such a manner, that the plane of the part-circle of the needle is approximately perpendicular to a longitudinal axis of the needle holder. The tip of the needle is then stuck into the tissue by means of a rotation of the needle holder with respect to its longitudinal axis. Due to the particularly high torque that can be transmitted by the inventive endoscopic instrument system to the tool and in this way to the needle held, a surgical suture can be conducted through a flexible endoscope in the way customary in laparoscopy, i.e. with customary endoscopic suture material and a half-round needle, in particular. In this way, in conducting endoscopic interventions via a natural access path according to the NOTES method, in particular the disadvantages connected to employing clips or clamps can be avoided, and in a much higher number of cases it is at all possible to close the incision made in the wall of the access organ.

In particular, the tool may be advantageously designed for gripping and holding a surgical needle. Such an endoscopic instrument designed as a needle holder in particular permits gripping and holding a surgical needle, and by means of a rotation with respect to a longitudinal axis of the instrument, sticking the needle into tissue and partly moving the needle through the tissue, releasing the needle, gripping the needle again in a portion which has already been moved through the tissue, and pulling a thread connected to the needle completely through the tissue. The design of the endoscopic instrument with an instrument shaft designed as a continuous tube permits the transmission of particularly high forces for actuating the tool, in which way the needle can be gripped with a high force and a turning away of the needle can be safely avoided. In this way, a particularly simple and safe operation of the needle holder for providing an endoscopic suture in the usual manner is made possible.

In order to grip and to hold a surgical needle, the tool may comprise two jaw members acting in an opposing manner with respect to each other, which is known in itself. One of the jaw members may be movable, for example, pivotable with respect to an axis transverse to the longitudinal axis of the instrument shaft, while the other jaw member is fixed in relation to the distal end of the instrument shaft. However, both jaw members may be movable with respect to the distal end of the instrument shaft, for example both jaw members may be pivotable symmetrically with respect to a common axis which is transverse to the longitudinal axis of the instrument shaft. Such an opening and closing of the jaw members can be controlled by the handle through the pull and/or push element. For safely gripping and holding the needle, the jaw members may comprise transverse ribs or grooves on their opposing surfaces, for example. In this way, a particularly simple operation and a safe execution of the suture are made possible. Advantageously, the tool with its two opposing jaw members may also or instead be designed for gripping and holding tissue.

According to a particularly preferred embodiment, at least a first section of the flexible tube exhibits a minimal bending radius which is smaller or equal to a minimal bending radius of the endoscope shaft in a first section of the endoscope shaft, wherein the first section of the flexible tube is arranged such that after introducing the endoscopic instrument into the endoscope for conducting the manipulations in the hollow space in the body, the first section of the flexible tube is situated in the first section of the endoscope shaft. The minimal bending radius here denotes that bending radius down to which the tube or the endoscope shaft, respectively, can be bent without a plastic deformation or, if a plastic deformation is permissible, at least without a rupture of the material and without, for example, buckling of the tube which would block or considerably narrow the lumen within the tube in which the pull and/or push element is arranged. Since re-usable instruments, in particular, are subject to multiple bending in various directions, while bending at a radius which is not less than the minimal bending radius preferably no fatigue of material should occur either. The minimal bending radius of the instrument shaft substantially is determined by the flexible tube and thus here is set equal to the bending radius of the flexible tube. The minimal bending radius of the endoscope shaft may be determined, for example, by a basic structure of the shaft, which, for example, may consist of pivotably connected elements as is known in itself. In a particularly advantageous manner, the minimal bending radius of the tube is smaller than the minimal bending radius of the respective section of the endoscope shaft by such an amount that with an excentric arrangement of the instrument channel in relation to a longitudinal axis of the endoscope shaft, the minimal bending radius of the tube is observed even if the endoscope shaft is bent in different directions.

Due to the minimal bending radius of the first section of the flexible tube being less than or equal to the minimal bending radius of the endoscope shaft in that section of the endoscope shaft in which the first section of the flexible tube is located when the manipulations are being conducted, it is made sure that, when the endoscope is bent due to the curvature of the access path or if such bending is enforced by steering the steerable section of the endoscope shaft, the flexible tube is not curved more than is possible without a rupture or another kind of damage. Thereby an increased safety of operation of the instrument system is achieved.

In a particularly advantageous manner, the first section of the flexible tube exhibits a minimal bending radius that is smaller than that of a second section of the flexible tube, which, for example, may be the remaining part of the flexible tube. As a design with a smaller minimal bending radius generally leads to a reduced rotational stiffness and/or a reduced torque that is transmissible, thereby it can be achieved that in those sections, where a small bending radius of the tube is not required, the tube is designed for providing a high rotational stiffness and/or a high transmissible torque. Thus, the minimal bending radius of the instrument shaft may be adjusted section-wise to the minimal bending radius of the endoscope. In this way, moreover, when a longitudinally directed force is exerted, the risk of buckling of the instrument shaft within the instrument channel, generally comprising a larger inner diameter than the outer diameter of the instrument shaft, can be precluded.

Thus, for example, the flexible tube can be designed to exhibit a large bending radius in a section, which, when the endoscopic instrument is inserted into the endoscope shaft, corresponds to a section in which the endoscope shaft exhibits a large bending radius and/or is subject to slight bending only, whereas the flexible tube may be designed with a smaller bending radius in sections which are subject to stronger bending in the inserted state. It is particularly advantageous that the section exhibiting the smaller minimal bending radius extends beyond the corresponding section of the endoscope by such a distance that even with a back and forth movement of the endoscopic instrument which is required for conducting the manipulations a bending load beyond the respective minimal bending radius is excluded.

According to a particularly preferred embodiment of the invention, the first section of the flexible tube is a distal end section of the flexible tube, and the first section of the endoscope shaft is the steerable end section of the endoscope shaft. In general, the steerable end section of the endoscope shaft exhibits a smaller bending radius than the remaining part of the endoscope shaft, being more frequently subject to bending in use, which bending may even occur in different directions. Due to the fact that the distal end section of the flexible tube exhibits a bending radius, which is smaller than that of the steerable end section of the endoscope shaft and which also may be smaller than that of the remaining parts of the bendable tube, unhindered steering of the distal end section of the endoscope shaft is made possible, such as for accessing different regions in a body cavity by deflection in different directions, for example.

In particular, the distal end section of the instrument shaft may have a length that corresponds to the length of the steerable end section of the endoscope shaft plus an advancement amount by which the tool must be advanced at least transitionally beyond the distal end of the endoscope shaft for performing the manipulations. In this way, an unobstructed use of the longitudinal movement is also made possible.

Preferably, the bending stiffness of the flexible tube in the first section, corresponding to the steerable end section of the endoscope shaft, also is smaller than in a second section. In this way, friction is reduced which would hinder a rotation of the instrument shaft with respect to its longitudinal axis in case of a bending of the steerable end section.

Preferably, the flexible tube comprises a third section exhibiting a smaller minimal bending radius and/or a smaller bending stiffness than the second section, the third section of the flexible tube being located about a proximal end section of the endoscope shaft when manipulations in the hollow space in the body are conducted. Many flexible endoscopes comprise a proximal entrance of the instrument channel that is arranged at an angle to the longitudinal axis of the shaft in the corresponding portion. The first and the second sections only need to overcome the angled portion when the endoscopic instrument is introduced into the instrument channel, and when it is withdrawn from the instrument channel when the endoscopic instrument is used, whereas the third section is moved multiply in the angled portion during use. Due to the smaller bending radius and/or the smaller bending stiffness in this section, it can thus be achieved that a multiple longitudinal motion and/or a rotational motion of the instrument shaft in the angled portion is made possible or facilitated.

The third section of the flexible tube, in particular, may be a proximally arranged end section of the tube to which the handle is attached. However, the third section may be followed in the proximal direction by a further section of the tube up to the handle.

Preferably, the endoscope comprises a straight guide tube arranged proximally, the instrument channel of the endoscope shaft leading into the guide tube. In particular, in this case, the flexible tube may comprise a fourth section arranged proximally with respect to the third section, the fourth section exhibiting a larger minimal bending radius and/or a higher bending stiffness than the third section of the flexible tube. Since the guide tube is straight, that section of the instrument shaft which during use of the instrument is located within the guide tube is not subject to bending, thus a design with a larger bending radius and/or a larger bending stiffness, respectively, is advantageous for achieving a higher rotational stiffness and/or the transmission of a higher torque. Moreover, canting due to longitudinal movement of the endoscopic instrument can be avoided in this way.

In particular, the minimal bending radius and/or the bending stiffness may be larger than in the second section of the tube, because the guide tube may have a larger inner diameter than the instrument channel in the endoscope shaft, the guide tube not being introduced into the body and thus not being subject to the corresponding limitations.

Even in the inserted state of the endoscopic instrument, the handle may be situated at a distance from a proximal entrance of the instrument channel and/or the guide tube. In this case, an increased bending stiffness may serve to facilitate operation and to avoid kinking the instrument shaft.

Preferably, the flexible tube is assembled of tube sections of different materials and/or with different outer diameters. By different materials as well as by different outer diameters of the tube, different minimal bending radii can be achieved. Furthermore, the wall thicknesses of the various sections of the tube may differ in order to achieve different bending stiffnesses.

Preferably, the tube sections may be connected to each other by welding, in particular laser welding, and/or hard soldering and/or gluing. In particular, the inner diameter of a tube section with larger outer diameter can be chosen such that it can be slid on a tube section with a smaller outer diameter and can be connected to the latter by welding or hard-soldering. In this way, a sufficiently durable connection is achieved, which is resistant against temperature-related and chemical effects and which is rotationally stiff. Furthermore, in welding as well as in hard-soldering, the concave fillet resulting from connecting tubes of different outer diameters may be filled. Alternatively or additionally, a surface in the connecting section may be ground smooth in order to reduce friction and to avoid jamming in moving the instrument shaft. When gluing is performed by filling the ring-shaped gap between the differently sized tube sections with glue, the advantage is achieved that notch stresses and material degradation due to the thermal charge in welding or soldering may be reduced or avoided.

According to a preferred embodiment, the flexible tube and thus the instrument shaft exhibits section-wise different minimal bending radii, the flexible tube having a smaller outer diameter in a section with a smaller minimal bending radius, as compared to a section with a larger minimal bending radius. Alternatively or additionally, the flexible tube may consist of a material with an enhanced deformability or, assuming equal elasticity modules, with a higher tensile strength in a section with a smaller minimal bending radius, as compared to a section with a larger minimal bending radius. Since the minimal bending radius substantially depends on the outer diameter and the properties of the material employed, in this way the instrument shaft can be advantageously designed exhibiting different bending radii. Apart from the elasticity module of the material of the tube, the different bending stiffnesses may also be determined by variation of the wall thickness of the tube. The pull and/or push element preferably is designed flexible, for example by designing it as a pull rope or as pull and/or push rod made of an elastic metal, in such a manner, that the minimal bending radius of the pull and/or push element always is less or at least not substantially larger than that of the tube. Depending on the embodiment, the pull and/or push element may also contribute to the bending stiffness of the instrument shaft.

Preferably, the minimal bending radius of the tube is the minimal elastic bending radius, i.e. such a bending radius down to which the tube can be bent without plastic deformation. In this way, it is ensured that friction arising during movement of the endoscopic instrument within the instrument channel bent by bending the endoscope, in particular friction during rotation with respect to its longitudinal axis, is as small as possible and independent on previous movements and does not depend on the direction of bending of the endoscope shaft. Moreover, material fatigue can be precluded more safely by avoiding a plastic deformation.

Suitable materials the flexible tube may consist of at least section-wise are, for example, spring steel, phynox and superelastic metals, such as for example nitinol. However, the flexible tube may also be made of stainless steel or of other metallic or even ceramic materials, for example of zirconium oxide ceramic. High deformability ensuing in a small bending radius, however accepting plastic deformations, may also be achieved by employing monel.

It is to be understood that the above mentioned features as well as the features to be explained below may not only be employed in the combinations mentioned, but also in other combinations or in isolation without leaving the scope of the present invention.

BRIEF DESCRIPTION OF THE DRAWINGS

Further aspects of the invention ensue from the following description of preferred embodiments and the drawing. The figures show.

DETAILED DESCRIPTION OF THE INVENTION

Figure 1A:
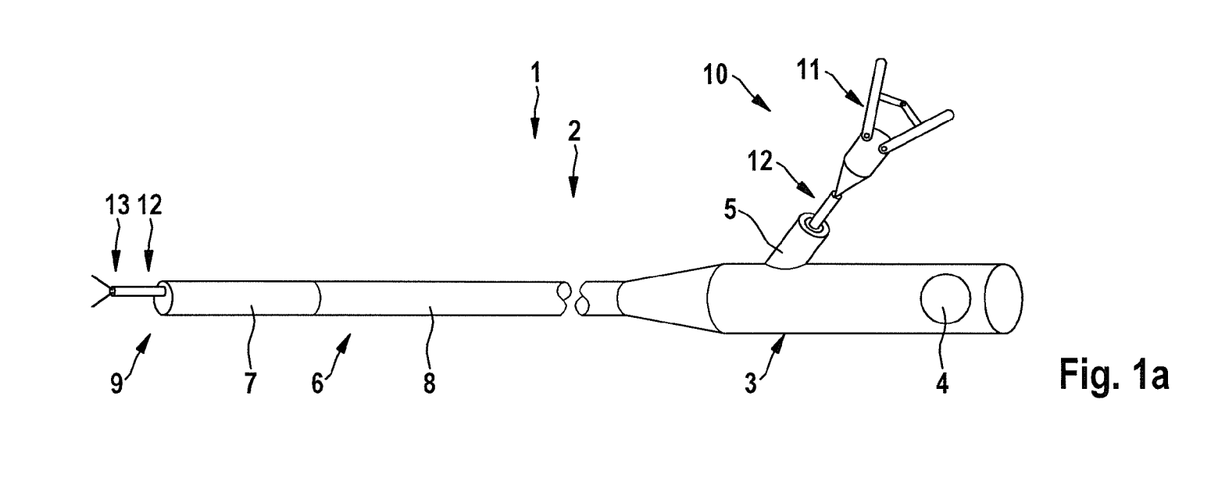
FIGS. 1a and 1b an endoscopic instrument system according to the invention.

An inventive endoscopic instrument system 1 comprises a flexible endoscope 2 and an endoscopic instrument 10, the endoscope 2 being depicted in FIG. 1*a* in a straight state. The endoscope 2 comprises an endoscope handle 3 exhibiting an actuation element 4 for steering a deflection, depicted symbolically, and a guide tube 5, as well as an endoscope shaft 6. The endoscope shaft 6 comprises a distal end section 7 and a proximal section 8 that may extend over the total remaining length of the endoscope shaft 6 and may be considerably longer than the distal end section 7. Within the endoscope shaft 6, an instrument channel extends, being continued into the endoscope handle 3, there leading into the guide tube 5 attached to it at an angle. The endoscopic instrument 10 consists of a handle 11, an elongate instrument shaft 12, and a tool 13. The instrument shaft 12 is formed by a flexible tube, within which a pull element extends between handle 11 and tool 13.

Figure 1B:
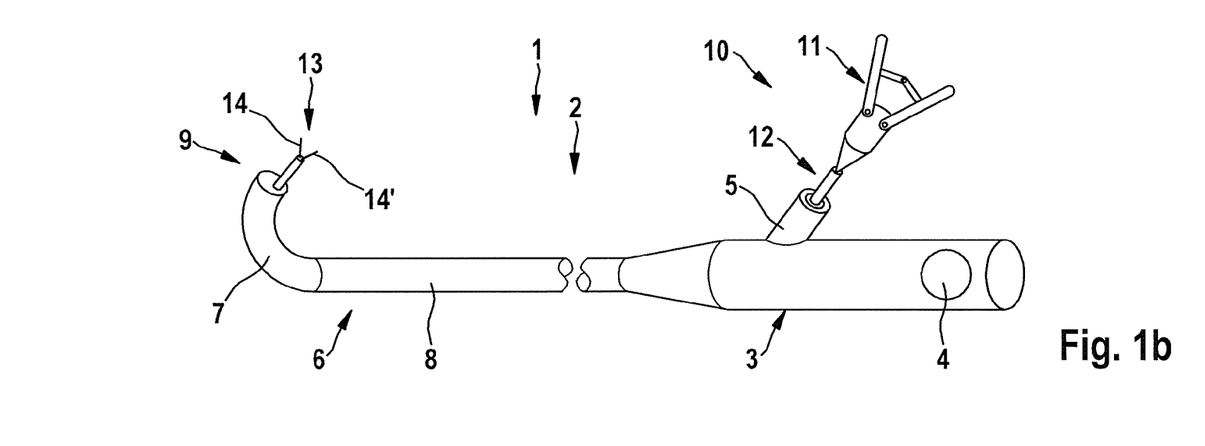

In FIG. 1*b*, the endoscopic instrument system shown in FIG. 1*a* is depicted in a deflected state. For this purpose, by means of the actuation element, wires or ropes extending within the endoscope shaft 6 can be pulled, effecting a deflection of the distal end section 7 of the endoscope shaft 6. In particular, the distal end section 7 may comprise a supporting structure formed of pivotably connected shaft segments guiding the wires or ropes, the movability of which segments determining a minimal bending radius of the distal end section 7. The distal end section 7 or the endoscope shaft 6 as a whole may be surrounded by a flexible covering, which may be a tube of a plastic material, for example.

In the situation shown in FIGS. 1*a* and 1*b*, the instrument shaft 12 and the tool 13 arranged at its distal end have been introduced into the guide tube 5 and the instrument channel following it. By actuating the handle 11 arranged at the proximal end of the endoscope acting on the pull element movable within the instrument shaft 12 by a mechanism only symbolically depicted in FIG. 1*a*, the tool 13 can be operated. For introducing the endoscopic instrument 10 into the instrument channel the tool 13 can be brought into a closed position (not shown).

As indicated by the opened jaw members 14, 14' in FIG. 1*b*, the tool 13 can also be operated in the deflected state of the distal end section 7 of the endoscope shaft 6, such that when designed as a needle holder, for example, a needle can be gripped and held. The minimal bending radius of the instrument shaft 12 in that section which is situated inside the steerable distal end section 7 is less than or equal to the minimal bending radius of the distal end section 7, thus enabling unlimited use of the endoscopic instrument 10. The section of the instrument shaft 12 that, when introduced, is situated within the proximal section 8 of the endoscope shaft 6, needs less flexibility as compared to the distal end section 7, and may, on the other hand, be designed with a larger minimal bending radius. This provides advantages concerning rotational stiffness and torque transmission by rotating the handle 11 with respect to the longitudinal axis of the proximal end portion of the instrument shaft 12, thus effecting a rotation of the tool 13 with respect to the longitudinal axis of the distal end portion of the instrument shaft 12 which is exact and may be performed with a high torque. For this purpose, the handle 11 as well as the tool 13 are connected to the tube forming the instrument shaft 12, such that they are rotationally fixed with respect to the respective longitudinal axis.

Moreover, the bending stiffness of the instrument shaft 12 in that section that is situated in the distal end section 7 of the endoscope shaft 6 may be reduced with respect to that section situated within the proximal section 8, in order to reduce the friction occurring with a movement of the instrument shaft 12 in the instrument channel. For reduction of friction, furthermore, an irrigation connector leading into the instrument channel may be provided at the guide tube 5 (not shown).

Figure 2:
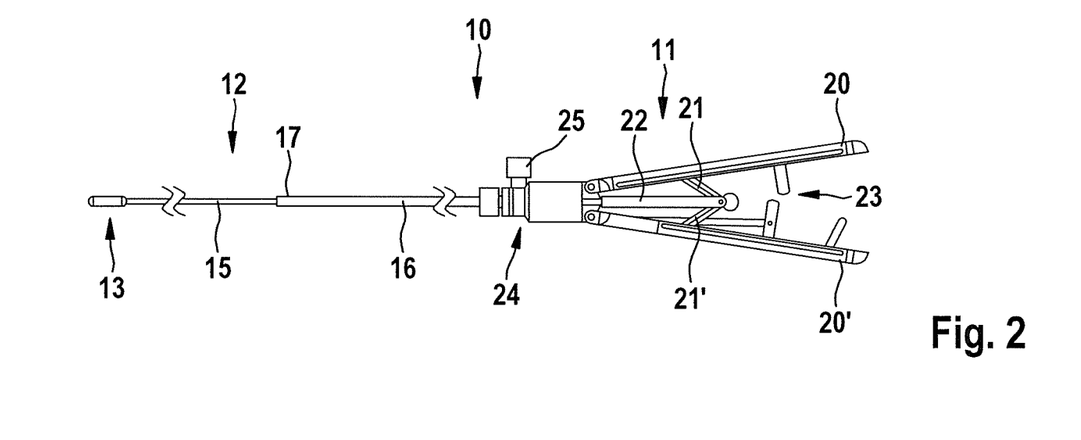
FIG. 2 an endoscopic instrument according to a first embodiment of the invention.

An inventive endoscopic instrument 10 is shown in total in FIG. 2. The instrument shaft 12 comprises a first, distal section 15, the length of which approximately corresponds to the length of the steerable end section 7, and a second section 16 comprising the total remaining length of the instrument shaft up to the handle 11 in the embodiment shown in FIG. 2. As depicted symbolically in FIG. 2, the first section 15 exhibits a smaller outer diameter than the second section 16. If both sections are made of the same material, the minimal bending radius of the first section 15 will be smaller than that of the second section 16. Both shaft sections 15, 16 are connected to each other in a connecting section 17.

The handle 11 comprises two handgrips 20, 20' arranged on a base element 24 inclined at a small angle with respect to a prolongation of the longitudinal axis of the instrument shaft 12, wherein the handgrips 20, 20' can be compressed against a spring force for actuating the tool 13, a tensile force being exerted on the pull element by levers 21, 21' and by a transmission element 22 connected to the pull element, such that the pull element can be shifted with respect to the instrument shaft 12. Thus, by actuating the handgrips 20, 20', the jaw members 14, 14' of the tool 13 can be opened or closed. For holding a gripped needle more securely, for example, a releasable detent 23 is provided for fixing the handgrips 20, 20' in a closed or partly closed position. Moreover, an irrigation connector may be present, covered by a cover lid 25 in FIG. 2.

The pull element guided within the instrument shaft 12, may be sealed against the latter by seals within the distal and the proximal end portions of the instrument shaft 12 (not shown). For this purpose, one or several O rings may be provided in the distal as well as in the proximal end portions, being sealingly arranged between the instrument shaft 12 and the pull element; however, for this purpose there may be provided a bellow-like foldable welded tube, in particular in the distal end portion. Checking the leak-tightness of the endoscopic instrument 10 may be possible in that case by a ventilation valve arranged in the proximal end portion of the instrument shaft 12 on a distal side of the proximal seal, for example.

Figure 3:
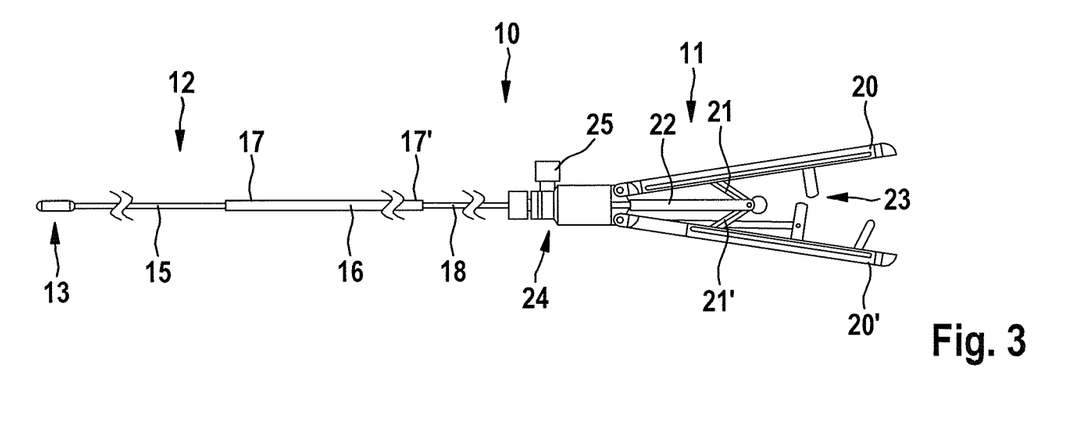
FIG. 3 an endoscopic instrument according to a second embodiment of the invention.

In the variation shown in FIG. 3, the instrument shaft 12 comprises a third section 18 arranged proximally with respect to the second section 16 and which, when the endoscopic instrument 10 has been introduced, is located about the junction of the instrument channel to the angulated guide tube 5, the junction being located within the endoscope handle 3. The third section 18 exhibits an outer diameter that is reduced with respect to the second section 16 and is connected to the second section 16 by a connecting section 17'. Due to the reduced outer diameter of the third section 18, a reduced minimal bending radius and a reduced bending stiffness are achieved in that portion in which the instrument shaft 12 has to overcome the curvature from the guide tube 5 into the instrument channel, thereby improving handling of the endoscopic instrument 10. Because only the distal and proximal sections 15, 18 exhibit a reduced diameter, transmission of a maximal torque and a maximal rotational stiffness are ensured. For the rest, the embodiment depicted in FIG. 3 is designed as the one shown in FIG. 2.

Figure 5:
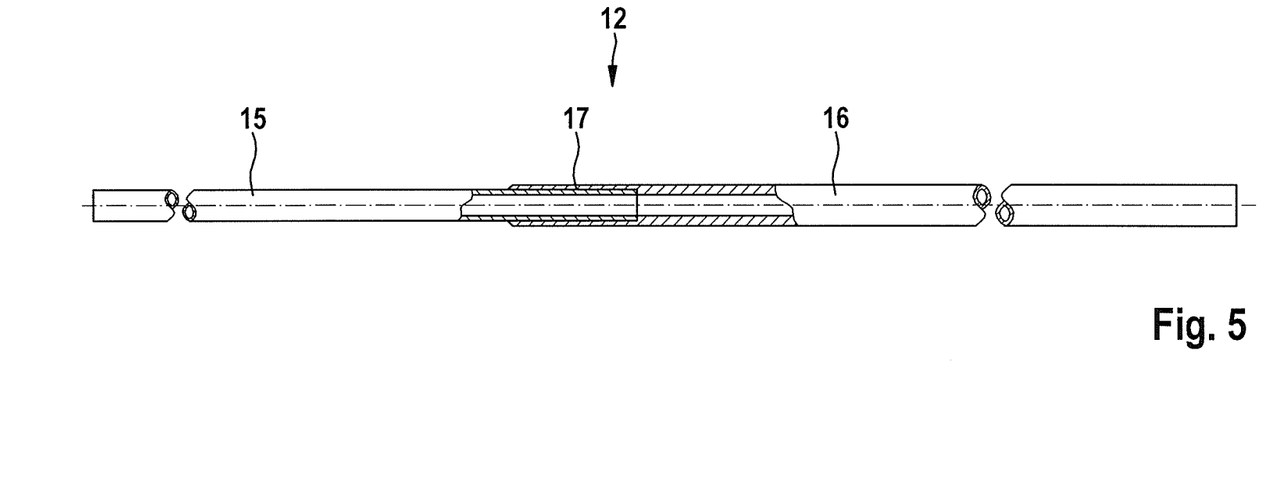
FIG. 5 is a flexible tube of an instrument according to the invention.

In FIG. 5, a flexible tube of an inventive instrument is shown in a partially cut longitudinal sectional view. The first section 15 exhibits an outer diameter that is reduced with respect to the second section 16 and thus exhibits a reduced minimal bending radius. The first section 15 may be formed, for example, by a phynox tube, and the second section by a stainless steel tube. In the connecting section 17, the tube sections are slid over one another and connected to each other for example by laser welding or hard-soldering. In that part of the second section 16 that is not slid over the tube of the first section 15, the tube of the second section 16 exhibits the same inner diameter as that of the first section in order to provide for a low-friction movement of the pull element guided in the tube, the pull element not being shown. The total continuous flexible tube may as well consist of several sections, for example of two phynox tubes and two stainless steel tubes of possibly different diameters.

Figure 4:
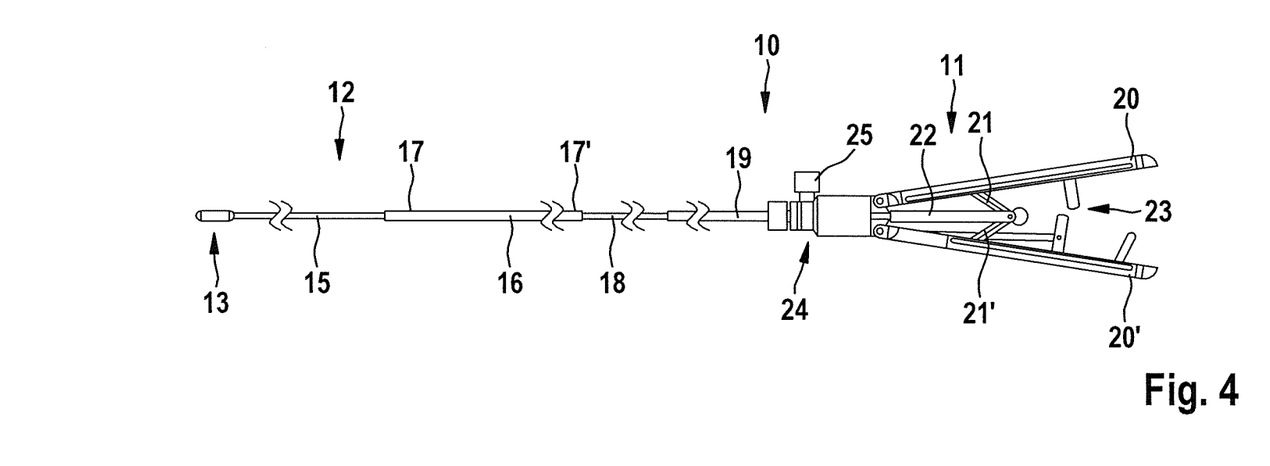
FIG. 4 is an endoscopic instrument according to a third embodiment of the invention.

In the variation shown in FIG. 4, the instrument shaft 12 comprises a third section 18 and a fourth section 19 arranged proximally with respect to the second section 16. The third section, when the endoscopic instrument 10 has been introduced, is located about the junction of the instrument channel to the angulated guide tube 5, the junction being located within the endoscope handle 3. The fourth section 19 exhibits an outer diameter that is increased with respect to the third section 18 and exhibits a larger minimal bending radius and/or a higher bending stiffness than the third section of the flexible tube. Due to the reduced outer diameter of the third section 18, a reduced minimal bending radius and a reduced bending stiffness are achieved in that portion in which the instrument shaft 12 has to overcome the curvature from the guide tube 5 into the instrument channel, thereby improving handling of the endoscopic instrument 10. Because only the sections 15, 18 exhibit a reduced diameter, transmission of a maximal torque and a maximal rotational stiffness are ensured. For the rest, the embodiment depicted in FIG. 4 is designed as the one shown in FIGS. 2 and 3.

According to advantageous embodiments of the invention, the length of the endoscope shaft 6 preferably amounts to more than about 400 mm, depending on its application, and in particular for NOTES operations through the stomach wall amounts to more than about 1000 mm. The instrument channel exhibits an inner diameter of about 1.7 to 4.2 mm (corresponding to about 5 to 13 Charrière), for example. The minimal bending radius of the endoscope shaft 6 in the portion of the distal end section 7 is about 25 mm to about 60 mm, preferably 30 mm to 40 mm, and is larger in the remaining sections of the endoscope shaft, for example about 100 mm.

The length, the outer diameter and the minimal bending radius of an endoscopic instrument to be used with the endoscope, are adapted to the respective endoscope. The instrument shaft 12 consists of a continuous flexible tube with an outer diameter of 1.2 mm or 1.4 mm, for example. When phynox or spring steel is employed, a minimal elastic bending radius of about 60 mm is achieved, when nitinol is employed, about 30 to 40 mm; if the outer diameter of the tube is 0.8 mm and spring steel is employed, the minimal bending radius is about 40 mm. When being used in the flexible endoscope, in each case a marginal plastic deformation can be accepted. The wall thickness of the flexible tube amounts to about 0.05 mm to 0.5 mm, and its length amounts preferably to more than 400 mm, in particular to more than 1000 mm.

In an endoscopic operation in the abdominal cavity performed according to the NOTES method, the endoscope 2 is introduced under endoscopic view through a natural access path, for example through the pharynx, the esophagus and the stomach. In doing so, the distal end section 7 is steered correspondingly in order to facilitate introduction. The endoscopic instrument 10 being designed, for example, as a needle holder at this time has not yet been introduced into the endoscope. By means of a cutting tool introduced through an instrument channel, an incision is made in the stomach wall. Thereafter, the endoscope 2 is introduced through this incision into the abdominal cavity. By means of gas insufflation, a hollow space can be created in which the actual endoscopic operation is performed, for which purpose further instruments can be introduced such as gripping tongues, biopsy tongues, scissors, electrodes, retrieval baskets, etc. However, it is also possible that only a diagnostic intervention is performed for which no further surgical manipulations are required. By deflecting the distal end section 7 of the endoscope shaft 6, the direction of viewing and working can be chosen according to the respective requirements. At the same time, illumination can be provided by illumination optics contained in the endoscope as well as image capturing by a CCD camera arranged in the distal or in the proximal portion of the endoscope.

After the actual intervention has been finished, the endoscope and, possibly, the inserted instruments, are withdrawn from the abdominal cavity through the incision into the stomach. In order to close the incision, now an endoscopic instrument designed as a needle holder is introduced, preferably when the endoscope shaft 6 is as straight as possible. Where required, the distal end section 7 of the endoscope shaft 6 is deflected as soon as the tool 13 with the jaw members 14, 14' protrudes from the distal end 9 of the endoscope shaft. By means of the jaw members 14, 14' of the needle holder, a half-round needle that also has been introduced, is gripped in its rear part close to the thread connected to the needle. Now, the tip of the needle protrudes laterally by about 10 to 15 mm with respect to the jaw members 14, 14'. Now the tip is stuck into the margins of the incision that are to be connected to each other by rotating the instrument shaft 12, until the tip of the needle emerges from the tissue. The handle 11 is actuated correspondingly for gripping and placing the needle and for rotating the instrument shaft 12. The torque required for moving the needle is created by a rotation of the handle 11 and transmitted by the continuous tube forming the instrument shaft 12 to the jaw members 14, 14' holding the needle. For exerting the required forces on the tissue, in this case the endoscope may serve as a counter-bearing, in particular its steerable distal end section 7, which can be held sufficiently stiff by the steering mechanism and which is supported on a relatively large area.

The tip of the needle is gripped by a further instrument, for example by gripping tongues. Thereafter, the rear part of the needle is released by the needle holder and the needle tip is gripped by the needle holder. The needle then is pulled out of the tissue. In the next step, the thread is pulled through the tissue until its loose end comprises only sufficient thread for forming a knot. This process is repeated if necessary, and a knot is formed endoscopically in the customary way. Thereafter, that end of the thread connected to the needle, is cut off. For this purpose, one or several further instruments may be required, which can be introduced through further instrument channels where necessary. In a corresponding manner thereafter the next knot can be formed.

After the suture has been provided, the endoscope with the endoscopic instrument is withdrawn from the natural access path.

For clarity, not all reference numerals are shown in all figures. Reference numerals not explained with respect to one figure have the same meaning as in the other figures.

What is claimed is:

1. An endoscopic instrument system, comprising:
   a flexible endoscope with an endoscope handle and an elongate endoscope shaft introducible into a hollow space in a body, the endoscope shaft having an instrument channel extending therethrough, and a bendable first section and a bendable second section each exhibiting a respective minimal bending radius, the minimal bending radius of the first section being smaller than the minimal bending radius of the second section, the first section being a steerable distal end section of the endoscope shaft;
   an endoscopic instrument with a handle;
   an elongate instrument shaft having a continuous flexible tube, the flexible tube having a bendable first section and a bendable second section, each exhibiting a respective minimal bending radius, the minimal bending radius of the first section being smaller than the minimal bending radius of the second section; and
   a tool actuatable by a push and/or pull element arranged within the instrument shaft, the push and/or pull element connected to the handle and to the tool;
   wherein the endoscopic instrument is configured to be introduced into the instrument channel for conducting manipulations in the hollow space in the body, such that the first section and the second section of the flexible tube are located at least partially within the instrument channel;
   wherein the flexible tube of the instrument shaft is connected, such that it is rotationally fixed, to the handle and to the tool with respect to a longitudinal direction of the flexible tube, such that rotation of the handle rotates the tool with respect to a longitudinal axis of the flexible tube;
   the minimal bending radius of the first section of the flexible tube is correlated to the minimal bending radius of the first section of the endoscope shaft, and the minimal bending radius of the second section of the flexible tube is correlated to the minimal bending radius of the second section of the endoscope shaft.

2. The endoscopic instrument system of claim 1, further comprising a surgical needle held by the tool.

3. The endoscopic instrument system of claim 1, wherein the tool includes two jaw members configured to act in an opposing manner with respect to each other.

4. The endoscopic instrument system of claim 1, wherein the first section of the flexible tube is configured to be situated in the first section of the endoscope shaft while conducting the manipulations in the hollow space in the body.

5. The endoscopic instrument system of claim 1, wherein the flexible tube comprises a third section exhibiting a minimal bending radius that is smaller than the minimal bending radius of the second section of the flexible tube, the third section of the flexible tube configured to be located about a proximal end section of the endoscope shaft during conducting the manipulations in the hollow space in the body.

6. The endoscopic instrument system of claim 5, wherein the endoscope comprises a straight guide tube into which the instrument channel of the endoscope shaft leads, and the flexible tube exhibits a fourth section being arranged proximally with respect to the third section, the fourth section exhibiting a minimal bending radius that is larger than the minimal bending radius of the third section of the flexible tube.

7. The endoscopic instrument system of claim 1, wherein the first section and the second section of the flexible tube are assembled of different materials and/or with different outer diameters relative to one another.

8. The endoscopic instrument system of claim 7, wherein the first section and the second section of the flexible tube are connected to each other by welding and/or hard-soldering and/or gluing.

9. The endoscopic instrument system of claim 1, wherein the first section of the flexible tube has an outer diameter that is smaller than an outer diameter of the second section of the flexible tube.

10. The endoscopic instrument system of claim 1, wherein the flexible tube consists of a material with a higher deformability or, if elasticity modules are equal, a higher tensile strength in a section with a smaller minimal bending radius than in a section with a larger minimal bending radius.

11. The endoscopic instrument system of claim 1, wherein each of the respective minimal bending radii is a minimal elastic bending radius.

12. The endoscopic instrument system of claim 1, wherein at least a portion of the flexible tube is made from spring steel, phynox and/or a superelastic metal.

13. The endoscopic instrument system of claim 1, wherein rotation of the handle is configured to create torque required for rotation of the tool, and the flexible tube is configured to transmit the torque to the tool.

14. The endoscopic instrument system of claim 1, wherein the handle comprises two handgrips arranged on a base element.

15. The endoscopic instrument system of claim 14, wherein the two handgrips are included at a small angle with respect to a prolongation of the longitudinal axis of the instrument shaft, and wherein the two handgrips are compressed against a spring force for actuation of the tool.

16. The endoscopic instrument system of claim 15, wherein a tensile force is exerted on the push and/or pull element by one or more levers and by a transmission element connected to the push and/or pull element, such that the push and/or pull element can be shifted with respect to the instrument shaft.

17. The endoscopic instrument system of claim 14, further comprising a releasable detent for fixing the two handgrips in a closed or partly closed position.

18. The endoscopic instrument system of claim 1, further comprising an irrigation connector covered by a cover lid.

19. A system, comprising:
   an endoscope with an endoscope handle and an endoscope shaft, the endoscope shaft having an instrument channel extending therethrough, and a bendable first section and a bendable second section each exhibiting a respective minimal bending radius, the minimal bending radius of the first section being smaller than the minimal bending radius of the second section, the first section being a steerable distal end section of the endoscope shaft; and
   an endoscopic instrument having:
      a handle;
      a tool;

a continuous flexible tube connected between and rotationally fixed relative to the handle and the tool, the continuous flexible tube having a first section and a second section, each exhibiting a respective minimal bending radius, the minimal bending radius of the first section being smaller than the minimal bending radius of the second section, the first section and the second section being located at least partially within the instrument channel of the endoscope shaft;

an actuation element disposed within the continuous flexible tube and connected to the handle and the tool;

wherein the minimal bending radius of the first section of the continuous flexible tube is correlated to the minimal bending radius of the first section of the endoscope shaft, and the minimal bending radius of the second section of the flexible tube is correlated to the minimal bending radius of the second section of the endoscope shaft.

20. The system of claim 19, wherein the actuation element is at least one of a push element and a pull element.

* * * * *

UNITED STATES PATENT AND TRADEMARK OFFICE
CERTIFICATE OF CORRECTION

| | | |
|---|---|---|
| PATENT NO. | : 9,433,342 B2 | Page 1 of 1 |
| APPLICATION NO. | : 13/312477 | |
| DATED | : September 6, 2016 | |
| INVENTOR(S) | : Silvana Perretta et al. | |

It is certified that error appears in the above-identified patent and that said Letters Patent is hereby corrected as shown below:

In the Claims

Col. 13, line 44:
"the minimal bending radius of the first section of the"

should read:
--wherein the minimal bending radius of the first section of the--

Signed and Sealed this
Fifteenth Day of November, 2016

Michelle K. Lee
*Director of the United States Patent and Trademark Office*